United States Patent [19]

Gurmarnik

[11] Patent Number: 5,312,374
[45] Date of Patent: May 17, 1994

[54] DEVICE FOR ADMINISTRATION OF EPIDURAL ANESTHESIA

[76] Inventor: Simon Gurmarnik, 38 Garrison Rd., #1, Brooklyne, Mass. 02146

[21] Appl. No.: 40,833

[22] Filed: Mar. 31, 1993

[51] Int. Cl.⁵ .............................................. A61M 5/00
[52] U.S. Cl. ................................. 604/264; 604/117; 604/158
[58] Field of Search ............... 604/116, 117, 164, 156, 604/173, 264, 280, 49, 51, 27, 28, 207, 218, 187, 189; 128/898, 774

[56] References Cited

U.S. PATENT DOCUMENTS 4,760,847 8/1988 Vaillancourt ........................ 606/185
4,863,423 9/1989 Wallace ................................ 604/48
5,106,376 4/1992 Mononen et al. .................... 604/164

Primary Examiner—C. Fred Rosenbaum
Assistant Examiner—V. Alexander
Attorney, Agent, or Firm—I. Zborovsky

[57] ABSTRACT

A needle cover of an epidural needle for epidural anesthesia with the use of an epidural catheter first insertable into the needle and then into a patient when the needle is removed, has two scales including a shorter scale provided on one side of the needle cover and having a length corresponding to a length of the epidural needle and a longer scale provided on another side of the needle and being longer than said shorter scale by a length corresponding to a required length of the epidural catheter inside the epidural space.

2 Claims, 2 Drawing Sheets

DEVICE FOR ADMINISTRATION OF EPIDURAL ANESTHESIA

BACKGROUND OF THE INVENTION

The present invention relates to a device for administration of epidural anesthesia with an epidural catheter and an epidural needle.

It is known that a standard procedure for the continuous epidural anesthesia requires localization of the epidural space by the epidural needle, then insertion of the epidural catheter through the epidural needle, then removal of the epidural needle and positioning of the catheter within the epidural space. Proper positioning of the epidural space is 2.5-3 cm inside the epidural space, and this proper position will minimize occurrence of complications. Since the distance between the skin and the epidural space varies from 3 to 8 cm, every case requires a time consuming calculation of the length of the catheter with the graduated epidural needle and catheter.

It is known that in this procedure for a continuous epidural anesthesia when the epidural catheter is utilized, the catheter in the epidural space can be the cause of various iatrogenic complications. In order to avoid leaving too great a length in the lumbar epidural space during epidural anesthesia, graduated Tuochy needles can be used together with graduated epidural catheters. On the latter, a special marking shows that, when it reaches the needle hub, the catheter tip is at the needle bevel. Approximately 5-7 cm of the catheter length are introduced into the epidural space. The needle is removed and placed upside down next to the catheter with the hub in contact with the patient's skin. In this position the distance between the special marking on the catheter and the graduation on the needle which marks the skin level is equivalent to the length of the catheter in the epidural space. This distance and therefore the catheter length can then be reduced to about 4 cm by carefully withdrawing the catheter. Knowing exactly how much of the catheter is within the epidural space can be of particular importance whenever that space is uncommonly far from the patient's skin, due to obesity, edema, use of paramedian route or a very oblique angle of the needle in the sagittal plane. The above described method is quite complicated and it is to be understood that it is desirable to improve the same.

In the stressful atmosphere of the operating room the above specified measurements and calculations present unnecessary hardships and usually are done with a great degree of inaccuracy.

SUMMARY OF THE INVENTION

Accordingly, it is an object of the present invention to provide a device for epidural anesthesia with determination of required length of the epidural catheter for continuous epidural anesthesia, which avoids the disadvantages of the prior art.

In keeping with these objects and with others which will become apparent hereinafter, one feature of the present invention resides, briefly stated, in a needle cover unit for determination of a required length of an epidural catheter for continuous epidural anesthesia, in which the needle cover having two scales of different lengths, wherein one scale corresponds to a length of the epidural needle, while the other scale is longer than the one scale by a length corresponding to a required length of the epidural catheter inside the epidural space.

When the device is designed in accordance with the present invention it is substantially simpler to determine the required length of the epidural catheter by positioning the needle cover on the skin and then placing the epidural catheter so that it extends from the hub of the epidural needle and therefore its required length is determined on the second longer scale.

The device makes significantly simpler the determination of the required length of the epidural catheter.

In accordance with another feature of the present invention, a device for epidural anesthesia is proposed with needle cover unit in which the epidural needle is introduced into the epidural space, then the needle cover with above mentioned two scales is placed against the skin parallel to the epidural needle, and the catheter is positioned from the hub of the epidural needle along the longer scale so that the required length of the epidural catheter is immediately determined on the longer scale.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
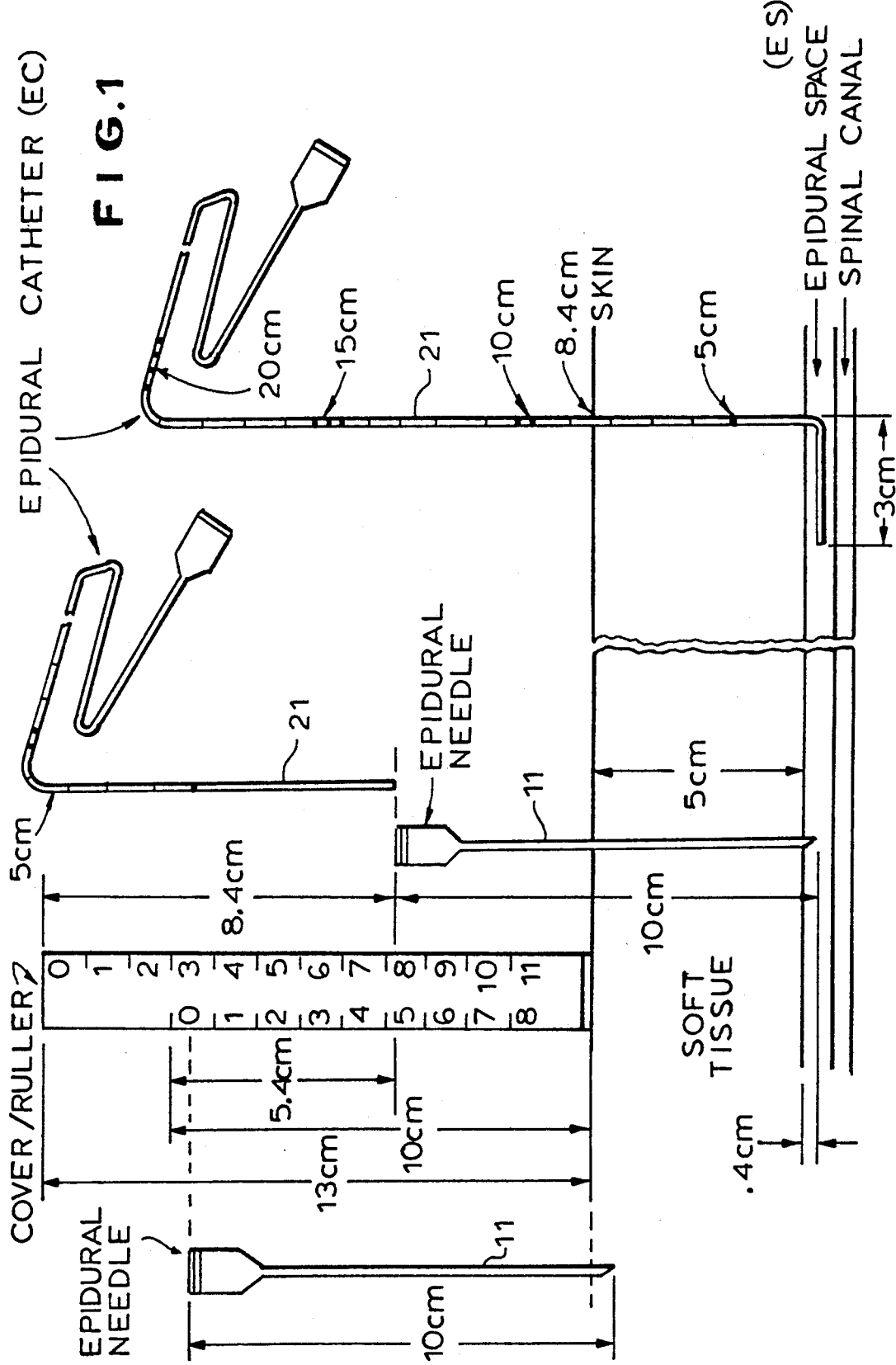
FIG. 1 is a view illustrating a method of determination of a required length of the epidural catheter for continuous epidural anesthesia.
Figure 2:
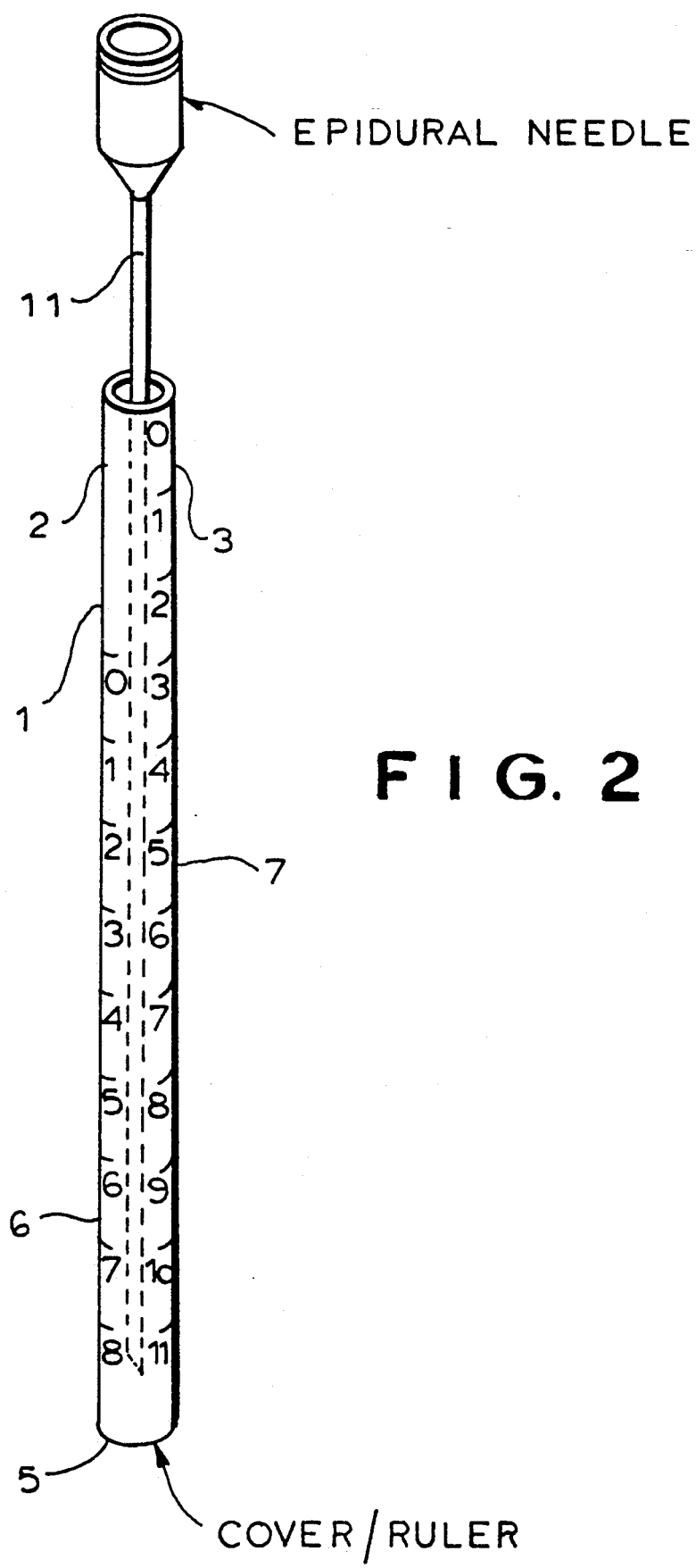
FIG. 2 is a view showing a needle cover of a needle cover unit of a device for epidural anesthesia with determination of the required length of the epidural catheter.

A device for continuous epidural anasthesia includes an epidural needle unit with an epidural needle identified with reference numeral 11 and a needle cover identified as 1. The cover is formed as an elongated member having two opposite sides 2 and 3, a top and a bottom 5. One side 2 of the cover is provided with a shorter scale 6 while the other side 3 of the cover is provided with a longer scale 7.

The bottom 5 of the cover 1 is used for placement of the cover against a skin. The shorter scale is substantially equal to the total length of the epidural needle. It is used for instant determination of the distance between the skin and the epidural space, or in other words the distance from zero on the shorter scale 6 to the hub of the epidural needle.

The longer scale 7 is longer than the epidural needle and is used for the instant determination of the required length of the epidural catheter 21. The longer scale 7 is longer than the shorter scale 6 by the required length of the epidural catheter inside the epidural space. The longer scale determines the required length of the epidural catheter which is equal to the distance from zero on the longer scale 7 to the hub of the epidural needle.

In the shown embodiment the shorter scale 6 is equal to 10 cm, while the longer scale 7 is equal to 13 cm, since the required length of the epidural catheter inside the epidural space is selected to be 3 cm.

The procedure of continuous epidural anesthesia with the device in accordance with the present invention is the same. In other words first the epidural space is localized by the epidural needle, then the epidural catheter is inserted through the epidural needle, then the epidural needle is removed, and the catheter is positioned within the epidural space. The determination of the required length of the catheter is performed in the following manner. When the epidural needle is inserted into the epidural space as shown in FIG. 1, the cover 1 is placed against the skin parallel to the epidural needle. Then the epidural catheter is positioned so that it extends from the hub of the epidural needle along the longer scale, and the required length of the epidural catheter can be immediately determined on the longer scale as shown in the drawings. In the shown example it has to be equal to 8 cm.

Thus, the needle cover in accordance with the invention simultaneously performs two functions, namely protecting the needle before its use and then forming a measuring device for the epidural catheter.

The same principle can be used with spinal needle, in which case only one scale is needed on the needle cover to indicate a skin-to-spinal canal distance.

While the invention has been described for epidural anesthesia, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A device for administering epidural anesthesia, comprising
    an epidural needle unit for localizing an epidural space and including an epidural needle and a needle cover removably attached to said needle, said needle being introducable through soft tissues into the epidural space;
    an epidural catheter insertable into the epidural space through said epidural needle to determine a required epidural catheter length for introducing said epidural catheter into the epidural space when said epidural needle is removed; and
    means for measuring the required length of the epidural catheter when the latter is inserted into said epidural needle, said measuring means including two scales provided on said needle cover and including a shorter scale provided on one side of said needle cover and having a length substantially corresponding to a length of said epidural needle and a longer scale provided on another side of said needle cover and being longer than said shorter scale by a length corresponding to a required length of said epidural catheter inside the epidural space, so that when said epidural needle is inserted in the epidural space and said needle cover is placed against a skin parallel to said epidural needle, then when said epidural catheter is placed parallel to said needle cover extending from a hub of said epidural needle along said longer scale, its length between the hub of said epidural needle and a beginning of said longer scale corresponds to a required length of said epidural catheter to be inserted into a patient, said shorter scale having a length of substantially 10 cm, while said longer scale has a length of substantially 13 cm.

2. An epidural needle unit for epidural anesthesia with the use of an epidural catheter, the epidural needle unit comprising
    an epidural needle which is insertable into an epidural space and through which an epidural catheter is inserted to determine a required length of the epidural catheter to be subsequently inserted after removal of said epidural needle; and
    a needle cover removable attached to said epidural needle and provided with two scales including a shorter scale provided on one side of said needle cover and having a length substantially corresponding to a length of said epidural needle and a longer scale provided on another side of said needle cover and being longer than said shorter scale by a length corresponding to a required length of the epidural catheter inside the epidural space, so that when said epidural needle is inserted in the epidural space and said needle cover is placed against a skin-parallel to said epidural needle, then when the epidural catheter is placed parallel to said needle cover extending from a hub of said epidural needle along said longer scale, its length between the hub of said epidural needle and a beginning of said longer scale corresponds to a required length of said epidural catheter to be inserted into a patient, said shorter scale having a length of substantially 10 cm, while said longer scale has a length of substantially 13 cm.

* * * * *